United States Patent
Rowe et al.

(10) Patent No.: US 10,821,092 B2
(45) Date of Patent: Nov. 3, 2020

(54) VISCOUS TOPICAL OCULAR FORMULATIONS

(71) Applicant: Encompass Development, Inc., Norcross, GA (US)

(72) Inventors: Thomas Rowe, Norcross, GA (US); Richard Coulon, Cumming, GA (US)

(73) Assignee: Encompass Development, Inc., Norcross, GA (US)

( * ) Notice: Subject to any disclaimer, the term of this patent is extended or adjusted under 35 U.S.C. 154(b) by 0 days.

(21) Appl. No.: 15/126,063

(22) PCT Filed: Mar. 17, 2015

(86) PCT No.: PCT/US2015/020973
§ 371 (c)(1),
(2) Date: Sep. 14, 2016

(87) PCT Pub. No.: WO2015/142853
PCT Pub. Date: Sep. 24, 2015

(65) Prior Publication Data
US 2017/0087117 A1 Mar. 30, 2017

Related U.S. Application Data

(60) Provisional application No. 61/954,103, filed on Mar. 17, 2014.

(51) Int. Cl.
| | | |
|---|---|---|
| *A61K 31/245* | (2006.01) | |
| *A61K 47/36* | (2006.01) | |
| *A61K 9/00* | (2006.01) | |
| *A61K 38/18* | (2006.01) | |
| *A61K 31/728* | (2006.01) | |

(52) U.S. Cl.
CPC .......... *A61K 31/245* (2013.01); *A61K 9/0048* (2013.01); *A61K 31/728* (2013.01); *A61K 38/1841* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 5,760,077 A | 6/1998 | Shahinian, Jr. | |
| 5,876,744 A | 3/1999 | Della Valle et al. | |
| 6,218,428 B1 * | 4/2001 | Chynn | A61K 9/0048 514/459 |
| 6,486,138 B1 * | 11/2002 | Asgharian | A61K 9/0048 514/54 |
| 2002/0183278 A1 | 12/2002 | Mastrodonato et al. | |
| 2005/0101582 A1 | 5/2005 | Lyons et al. | |
| 2007/0219170 A1 * | 9/2007 | Samson | A61K 9/0048 514/171 |
| 2008/0268051 A1 | 10/2008 | Hughes | |
| 2013/0172357 A1 | 7/2013 | Horn | |

OTHER PUBLICATIONS

European Search Report for Application 15764070.7, dated Sep. 8, 2017.

* cited by examiner

*Primary Examiner* — Elly-Gerald Stoica
(74) *Attorney, Agent, or Firm* — Nexsen Pruet PLLC; David Bradin

(57) ABSTRACT

Compositions and methods for providing anesthesia to the eye, for treating or preventing inflammatory disorders in the eye, or for treating or preventing ocular infections, are disclosed. The compositions include a glycosaminoglycan, such as hyaluronic acid, in a concentration suitable for achieving a desired viscosity, as well as an active agent, such as an anesthetic, anti-inflammatory, antimicrobial, antiproliferative, antimetabolite, prostaglandin, antioxidant, TGF-beta, or mitomycin C.

17 Claims, No Drawings

VISCOUS TOPICAL OCULAR FORMULATIONS

CROSS REFERENCE TO RELATED APPLICATIONS

This application claims priority under 35 U.S.C. 371 to PCT/US15/20973, filed on Mar. 17, 2015, which turn claims to priority to U.S. Provisional Application Serial No. 61/954,103, filed on Mar. 17, 2014. The contents of each of these applications is incorporated by reference in their entirety purpose.

FIELD OF THE INVENTION

The invention is generally in the area of formulations for use in treating ocular disorders, or for providing anesthesia to patients before, during, or after surgery or eye injuries. The formulations include glucosaminoglycans, such as hyaluronic acid, in a concentration sufficient to provide adequate viscosity to the formulations such that active agents applied to the eye remain on the surface of the eye or in the eye for a suitable period of time.

BACKGROUND OF THE INVENTION

There are many types of ocular disorders, which often require treatment applied directly to the eye. In such formulations, it is desired that the formulations have a suitable surface retention properties such as viscosity, such that the formulations stay on the eye for a suitable period of time to deliver desired medications.

The same is true during eye surgery. It is preferable that the eye is anesthetized before surgery, that anesthesia is maintained throughout surgery without additional applications of the topical anesthetic and, ideally, for a period of time after the surgery is completed.

SUMMARY OF THE INVENTION

Compositions and methods for providing active agents to the eye, and methods of using such compositions, are disclosed. The compositions, also referred to herein as formulations, include a glycosaminoglycan, such as hyaluronic acid, in sufficient amount to provide the compositions with a suitable viscosity to maintain the active agent on the eye or absorbed into the target ocular tissue for a desirable period of time after administration.

Where the glycosaminoglycan is hyaluronic acid with a molecular weight of around $10^6$ it is present in a concentration between about 0.25 and about 1.0 percent by weight in water, preferably between about 0.5 and about 0.9 percent by weight in water, and more preferably, between about 0.6 and about 0.75 percent by weight in water.

As the molecular weight increases, the viscosity increases as well. Accordingly, if the molecular weight of the HA is higher than $10^6$, the concentration should be adjusted to provide a viscosity in the range that the HA with a molecular weight of $10^6$ would have. The opposite holds true as the molecular weight is lower, so the concentration of HA would be increased to have the same viscosity as HA with a molecular weight of $10^6$ would have.

Where other glycosaminoglycans are used, the concentration is selected such that the formulations have a viscosity in the same range as that where HA with a molecular weight of $10^6$ is used in the above-listed weight ratios.

The compositions can be in the form of stabilized formulations (i.e., formulations which not require reconstitution with separately supplied sterile water), and formulations for reconstitution.

The compositions preferably have a pH in the range of between about 4.0 and about 7.0, more preferably from a pH of about 6.0 to about 6.5. The compositions can further include between about 0.4% and about 1.0% sodium chloride; between about 0.1% and about 2.0% citric acid; between about 0.1% and about 2.0% sodium citrate, between about 0.1% and about 10.0% of the active agent; and, in some embodiments, water.

The active agents include, but are not limited to, anesthetics, anti-inflammatory agents, anti-infective agents, anti-proliferative agents and combinations thereof.

Such stabilized or reconstituted formulations can be administered to the eye to provide anesthesia, to prevent or treat inflammation, to prevent unwanted cell proliferation and/or to provide treatment or prophylaxis of microbial infections. Particularly where eye surgery is performed, prophylaxis includes prevention of post-surgical infection.

Representative compositions include eye drops, or gels, and other topically applied ophthalmic formulations). In part due to the viscosity of the formulation, a therapeutically effective concentration of the active agent can remain in the tissue(s) for a considerable period of time. Accordingly, an advantage of certain compositions described herein is a simplified dosing regimen. For example, one or two topical applications may provide a sufficient tissue concentration that an effective concentration remains resident in the eye tissue for several hours. Thus, a complete treatment regimen may involve only one or two topical applications.

The topical compositions can be prepared, for example, by: (a) combining the glycosaminoglycans of a suitable molecular weight, in a suitable amount to provide a desired viscosity, with water and an active agent in a desired concentration, and then adjusting the solution to a pH of about 4.0 to about 7.0, or more preferably from a pH of about 6.0 to about 6.5). Where the active agent is tetracaine, the pH is preferably around 4.8.

The compositions can also include an additional viscosity-modifying agent, for example, a lightly crosslinked carboxyl-containing polymer, which causes the solution to undergo a rapid increase in viscosity upon a pH rise associated with administration to tissues, such as those of the eye and the surrounding region The compositions can also include an additional viscosity-modifying agent, for example, a lightly crosslinked carboxyl-containing polymer, which causes the solution to undergo a rapid increase in viscosity upon interaction with certain salts or enzymes associated with administration to tissues, such as those of the eye and the surrounding region. The addition of such viscosity-modifying agents allows for the use of less glycosaminoglycan, as long as the compositions remain within the desired viscosity range.

Representative types of eye surgeries for which the compositions can be used to provide anesthesia include laser eye surgery, refractive surgery, keratoplasty, keratotomy, keratomilleusis, cataract surgery, glaucoma surgery, canaloplasty, Karmra inlays, scleral reinforcement surgery, corneal surgery, vitreo-retinal surgery, retinal detachment repair, retinopexy, eye muscle surgery, surgery involving the lacrimal apparatus, insertion of implants into the eye, and eye removal.

Representative types of inflammatory ocular disorders that can be treated by topical application of the compositions, where the compositions include an anti-inflammatory agent, include wet and dry age-related macular degeneration (AMD), diabetic retinopathy (DR), glaucoma, neovascular glaucoma, retinal vasculitis, uveitis, such as posterior uveitis, conjunctivitis, retinitis secondary to glaucoma, episcleritis, scleritis, optic neuritis, retrobulbar neuritis, ocular inflammation following ocular surgery, ocular inflammation resulting from physical eye trauma, cataract, ocular allergy and dry eye.

Representative microbial infections that can be treated or prevented include viral, fungal, and bacterial infections in the eye, as well as ocular disorders resulting from these infections, such as trachoma, conjunctivitis, and the like. Representative bacteria that cause ocular infections in the inner or external eye include *Haemophilus, Neisseria, Staphylococcus, Streptococcus*, and *Chlamydia*.

Where an infection causes a disorder associated with an inflammatory component, the co-administration of anti-inflammatory agents and anti-microbials (i.e., anti-virals, anti-bacterials, anti-fungals, anti-parasitics, and the like), can be desirable. Other active agents, such as anti-proliferatives, anti-metabolites, VEGF inhibitors, prostaglandins, TGF-beta, mitomycin C, and antioxidants can also be added.

The present invention will be better understood with reference to the following detailed description.

DETAILED DESCRIPTION

In one embodiment, the invention described herein relates to topical compositions that include glycosaminoglycans, such as hyaluronic acid, at appropriate concentrations to provide a desired viscosity, along with active agents to provide anesthesia, to reduce inflammation, and/or to treat or prevent ocular infections and/or disorders caused by ocular infections. The compositions can be administered alone or in combination with one or more additional active agents suitable for providing anesthesia, treating or preventing inflammation, or treating or preventing ocular infections.

The present invention will be better understood with reference to the following detailed description, and with respect to the following definitions.

Definitions

The term "an effective amount" refers to the amount of active agent, alone or in combination with one or more additional active agents, needed to provide suitable anesthesia for a desired period of time, to provide appropriate anti-inflammatory effect, or to prevent the occurrence of, or eradicate, an ocular infection. Ideally, where the compositions are used to treat or prevent ocular infection, the compositions will eradicate the microbial cause and the inflammatory symptoms associated with various ocular disorders.

By "administering" is meant a method of giving one or more unit doses of an pharmaceutical composition to an animal, such as a human, topically to the eye. The actual method of administration may vary depending on various factors, e.g., the components of the pharmaceutical composition, the surgical site, the site of the potential or actual bacterial infection, the bacteria or other microbes involved, and the severity of the actual bacterial infection.

By "anesthesia" is meant providing anesthesia, with one or more administrations of the compositions described herein, to the ocular or periocular tissues for a sufficient period of time to carry out a surgical procedure, to provide relief for a patient while recovering from such a procedure, from ocular injuries, from ocular infections, from ocular inflammatory disorders, and/or from cellular proliferation in or around the eye.

By "ocular bacterial infection" is meant the invasion of an eye in a host animal by pathogenic bacteria. For example, the infection may include the excessive growth of bacteria that are normally present in or on the body of an animal or growth of bacteria that are not normally present in or on the animal. More generally, a bacterial infection can be any situation in which the presence of a bacterial population(s) is damaging to a host animal. Thus, an animal is "suffering" from an ocular bacterial infection when an excessive amount of a bacterial population is present in or on the animal's eye, or when the presence of a bacterial population(s) is damaging the cells or other tissue in the eye of the animal.

By "inflammatory disease" is meant a disease state characterized by (1) alterations in vascular caliber that lead to an increase in blood flow, (2) structural changes in the microvasculature that permit the plasma proteins and leukocytes to leave the circulation, and (3) emigration of the leukocytes from the microcirculation and their accumulation in the focus of injury. The classic signs of acute inflammation are erythema, edema, tenderness (hyperalgesia), and pain. Chronic inflammatory diseases are characterized by infiltration with mononuclear cells (e.g., macrophages, lymphocytes, and plasma cells), tissue destruction, and fibrosis. Non-limiting examples of inflammatory ocular diseases include trachoma, wet and dry age-related macular degeneration (AMD), diabetic retinopathy (DR), glaucoma, neovascular glaucoma, retinal vasculitis, uveitis, such as posterior uveitis, conjunctivitis, retinitis secondary to glaucoma, episcleritis, scleritis, optic neuritis, retrobulbar neuritis, ocular inflammation following ocular surgery, ocular inflammation resulting from physical eye trauma, cataract, ocular allergy and dry eye.

By "treating" is meant administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to improve the patient's condition. Thus, in the claims and embodiments, treating is the administration to a mammal either for therapeutic or prophylactic purposes.

The term "pharmaceutically acceptable salt" is used throughout the specification to describe any pharmaceutically acceptable salt form or active agents or derivatives thereof. Pharmaceutically acceptable salts include those derived from pharmaceutically acceptable inorganic or organic bases and acids. Citric acid is a specific example of a suitable acid. Suitable salts include those derived from alkali metals such as potassium and sodium, alkaline earth metals such as calcium and magnesium, among numerous other acids well known in the pharmaceutical art.

The present invention satisfies an existing need for topical compositions to provide extended administration times of active agents to the eye, relative to existing ocular compositions.

By providing an extended administration of the active agent, the active agent may be administered less frequently than with conventional topical ocular compositions. Accordingly, the treatment methods described herein may improve compliance, and shorten the course of treatment.

I. Types of Ocular Compositions

The ocular compositions described herein include a glycosaminoglycan, one or more active agents, and a suitable solvent. The formulations can optionally also include preservatives and other pharmaceutically-acceptable excipients commonly found in ocular formulations.

The compositions are intended for use in topical application to the eye, or to surrounding tissues.

The compositions typically have a viscosity in the range of between about 5 cps and 50,000 cps more preferably between about 50 cps and about 5,000, and, most preferably, between about 200 cps and about 1,000 cps The viscosity is provided by the glycosaminoglycans, though may also be provided by other viscosity-modifying agents, such as lightly crosslinked carboxyl-containing polymers.

Eye drops are useful in treating conditions affecting either the exterior surface of the eye or tissues in the front of the eye, and some formulations can penetrate to the back of the eye for treatment of retinal diseases.

In addition, suitably stable formulations can be dispensed for administration over an extended course of treatment, or packaged in single dose forms suitable for direct administration by a patient or physician without the effort or concern over reconstitution. Stable aqueous formulations can be administered topically In preferred embodiments of this invention, wherein the composition is intended for topical administration to ocular or periocular tissues, the composition may be formulated for application as a liquid drop, ointment, a viscous solution or gel, a ribbon, or a solid. The composition can be topically applied, for example, without limitation, to the front of the eye, under the upper eyelid, on the lower eyelid and in the cul-de-sac.

In an alternative embodiment the stabilized formulation is formulated as a solid, semi-solid, powdered, or lyophilized composition, which upon addition of water or aqueous solutions produces a stabilized formulation having a pH of about 4.8 to about 7.8, more preferably of about 5.8 to about 7.6 more preferably from about 6.5 to about 7.5, more preferably of about 6.8 to 7.2, and even more preferably about 7.0.

Representative formulations are described in detail below.

Formulations for Topical Administration

The active agents described herein are amenable to topical administration to eye and periocular tissues. The agents can be supplied to the eye surface in a variety of ways, including as an aqueous ophthalmic solution or suspension, as an ophthalmic ointment, and as an ocular insert, but application is not limited thereto. Any technique and ocular dosage form that supplies the active agent to the external eye surface is included within the definition of "topically applying." Although the external surface of the eye is typically the outer layer of the conjunctiva, it is possible that the sclera, cornea, or other ocular tissue could be exposed such as by rotation of the eye or by surgical procedure, and thus be an external surface. For the purposes of this application, periocular tissues are defined as those tissues in contact with the lachrymal secretions, including the inner surface of the eye lid, the tissues of the orbit surrounding the eye, and the tissues and ducts of the lachrymal gland.

The amount of active agent topically supplied is effective to provide anesthesia, treat or prevent inflammation, and/or treat or prevent infection in a tissue of the eye, or treat or prevent unwanted cellular proliferation in or around the ocular or periocular tissues.

For anesthesia, this means that the conditions of application result in a longer period of anesthesia, resulting in less frequent dosing during surgery, during patient recovery from surgery, for patient use while recovering from ocular injuries, ocular inflammatory disorders, or ocular infections, or for palliative therapy for patients suffering from unwanted cellular proliferation in or around the eye. For example, as shown in the working examples, an effective amount of an anesthetic such as tetracaine can be administered to the eye and provide anesthesia for up to 55 minutes.

For infection, this means that the conditions of application result in a retarding or suppression of the infection. Typically at least about $MIC_{50}$ for the targeted bacteria or parasite is delivered to the ocular tissue by the topical application of an effective amount. The amount of active agent actually supplied to the external eye surface will almost always be higher than the tissue concentration. This reflects the penetration hold up of the active agent by the outer tissue layers of the eye and that penetration is, to some extent, concentration and contact time driven. Thus, supplying greater amounts for longer periods of time to the exterior will drive more active agent into the tissues. This in turn will result in higher concentrations of the active agent in the affected tissues. The concentration of the active moiety can be increased to levels above the $MIC_{50}$. This increase in tissue concentration can extend the duration of the anti-infective effect. This duration of effect can be for a period of at least about 2 hours, or more preferably at least about hours, more preferably at least about 8 hours, or more preferably at least about 12 hours.

Where a series of applications are typically employed in a topical administration dosing regimen, it is possible that one or more of the earlier applications will not achieve an effective concentration in the ocular tissue, but that a later application in the regimen will achieve an effective concentration. This is contemplated as being within the scope of topically applying active agents in an effective amount. However, generally a single application, such as consisting of one or two drops, provides a therapeutically effective concentration (e.g. one that retards or suppresses the infection) of the active agents within a tissue of the eye. Indeed, although dependent on the amount and form of the ophthalmic composition, a single application will typically provide a therapeutically effective amount of the active agents within a tissue of the eye for at least about 2, more preferably about 4, more preferably about 8, more preferably about 12, and more preferably at least about 18 hours. As discussed above, the stabilized active agents compositions of this invention may be topically administered to the eye, to provide prophylaxis or treatment of infections.

Active agent compositions suitable for topical administration to the eye or periocular tissue can include one or more "ophthalmically acceptable carriers."

For anti-inflammatories, the concentration of the active moiety can be increased to levels above the minimum therapeutic concentration (MTC). This increase in tissue concentration can extend the duration of the anti-inflammatory effect. This duration of effect can be for a period of at least about 2 hours, or more preferably at least about hours, more preferably at least about 8 hours, or more preferably at least about 12 hours.

Where a series of applications are typically employed in a topical administration dosing regimen, it is possible that one or more of the earlier applications will not achieve an effective concentration in the ocular tissue, but that a later application in the regimen will achieve an effective concentration. This is contemplated as being within the scope of topically applying active agents in an effective amount. However, generally a single application, such as consisting of one or two drops, provides a therapeutically effective concentration (e.g. one that either retards or suppresses the upregulation of deleterious or negative responses to the treated condition, such as pain, continued or advancing infection, inflammation or proliferation of unwanted cellular structures or one that enhances or promotes the down regulation of positive or healing responses to the treated condition) of the active agents within a tissue of the eye. Indeed, although dependent on the amount and form of the ophthalmic composition, a single application will typically provide a therapeutically effective amount of the active agents within a tissue of the eye for at least about 2, more preferably about 4, more preferably about 8, more preferably about 12, and more preferably at least about 18 hours. As discussed above, the stabilized active agents compositions of this invention may be topically administered to a variety of tissues, including the eye, to provide prophylaxis or treatment of infections.

Active agent compositions suitable for topical administration to the eye or periocular tissue can include one or more "ophthalmically acceptable carriers."

II. Formulation Components

The individual components of the compositions are described in detail below:

Glycosaminoglycans

As used herein, "glycosaminoglycans," GAG or mucopolysaccharides refers to long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) or galactose. Glycosaminoglycans are highly polar and attract water.

Glycosaminoglycans vary in the type of hexosamine, hexose or hexuronic acid unit they contain (e.g. glucuronic acid, iduronic acid, galactose, galactosamine, glucosamine). They also vary in the geometry of the glycosidic linkage.

Glycosaminoglycans have high degrees of heterogeneity with regards to molecular mass, disaccharide construction, and sulfation. Examples of GAGs include chondroitin sulfate, dermatan sulfate, keratan sulfate, heparin, heparan sulfate, and hyaluronan.

Based on core disaccharide structures, GAGS are classified into four groups. Heparin/heparan sulfate (HSGAGs), chondroitin/dermatan sulfate (CSGAGs), keratan sulfate-types, and hyaluronic acid.

Heparin has the highest negative charge density of any known biological molecule.

Heparan sulfate is highly similar in structure to heparin, but heparan sulfate's disaccharide units are organized into distinct sulfated and non-sulfated domains.

Chondroitin sulfate is the most prevalent GAG. Chondroitin sulfate and dermatan sulfate, which comprise CSGAGs, are differentiated from each other by the presence of GlcA and IdoA epimers respectively. With respect to keratan sulfate-types, in the cornea and cartilage, the keratan sulfate domain of aggrecan (also known as cartilage-specific proteoglycan core protein (CSPCP) or chondroitin sulfate proteoglycan 1) consists of a series of tandemly repeated hexapeptides with a consensus sequence of E(E/L)PFPS. Additional keratan sulfated proteoglycans include lumican (LUM), keratocan, and mimecan (OGN).

The fourth class of GAG, hyaluronic acid (HA), is a linear polysaccharide composed of repeating disaccharide units of β-D-glucuronic acid and β-D-N-acetylgalactosamine, and has a very high molecular mass, ranging from $10^5$ to $10^7$ Da. HA is the only GAG that is exclusively non-sulfated.

Although any GAG can be used in the compositions described herein, HA is preferred. The preferred molecular weight for the HA is between about 900,000 Daltons and about 1,200,000 Daltons. The viscosity of the formulations is preferably between about 50 cps and about 1000 cps, More preferably between 200 cps and 850 cps and most preferably between 350 cps and 700 cps which is a viscosity provided by around 0.75% HA by weight.

Where the glycosaminoglycan is hyaluronic acid with a molecular weight of around $10^6$ it is present in a concentration between about 0.35 and about 1.0 percent by weight in water, preferably between about 0.5 and about 0.9 percent by weight in water, and more preferably, between about 0.6 and about 0.75 percent by weight in water. As the molecular weight increases, the viscosity increases as well. Accordingly, if the molecular weight of the HA is higher than $10^6$, the concentration should be adjusted to provide a viscosity in the range that the HA with a molecular weight of $10^6$ would have. The opposite holds true as the molecular weight is lower, so the concentration of HA would be increased to have the same viscosity as HA with a molecular weight of $10^6$ would have.

Where other glycosaminoglycans are used, the concentration is selected such that the formulations have a viscosity in the same range as that where HA with a molecular weight of $10^6$ is used in the above-listed weight ratios.

Aqueous Media and Appropriate Buffers

The aqueous compositions (solutions or suspensions) described herein preferably use water that has no physiologically or ophthalmically harmful constituents. Typically purified or deionized water is used. The pH is adjusted by adding any physiologically and ophthalmically acceptable pH adjusting acids, bases, or buffers to within a range which is both suitable to the API in the formulation and the GAG used for viscosity enhancement. Any of these drug-dependent pH ranges can be used with any of the compositions of the present invention, including, without limitation, intravenous and topical embodiments. Examples of acids include acetic, boric, citric, lactic, phosphoric, hydrochloric, and the like, and examples of bases include potassium hydroxide, sodium hydroxide, sodium phosphate, sodium borate, sodium citrate, sodium acetate, sodium lactate, tromethamine, THAM (trishydroxymethylamino-methane), and the like. Salts and buffers include but are not limited to citrate/dextrose, sodium bicarbonate, ammonium chloride and mixtures of the aforementioned acids and bases. The pH can be adjusted, for example, by adding sodium hydroxide.

Viscosity-Modifying Agents in the Form of Aqueous Polymeric Suspensions

In some embodiments, in addition to the glycosaminoglycans, an additional form of viscosity modifying agent can be used, so long as the viscosity stays within the ranges described herein. A preferred form of stabilized compositions including active agents for administration to the ocular and periocular tissues is an aqueous polymeric suspension. Here, at least one of the active agents or the polymeric suspending agent is suspended in an aqueous medium having the properties as described above. The active agents may be in suspension, although in the preferred pH ranges certain active agents will be in solution (water soluble), or both in solution and in suspension. It is possible for significant amounts of the active agents to be present in suspension.

The polymeric suspending agent is preferably in suspension (i.e. water insoluble and/or water swellable), although water soluble suspending agents are also suitable for use with a suspension of the active agents antibiotic. The suspending agent serves to provide stability to the suspension and to increase the residence time of the dosage form on the eye. It can also enhance the sustained release of the drug in terms of both longer release times and a more uniform release curve.

Examples of polymeric suspending agents include dextrans, polyethylene glycols, polyvinylpyrolidone, polysaccharide gels, Gelrite®, cellulosic polymers like hydroxypropyl methylcellulose, and carboxy-containing polymers such as polymers or copolymers of acrylic acid, as well as other polymeric demulcents. A preferred polymeric suspending agent is a water-swellable, water-insoluble polymer, especially a crosslinked carboxy-containing polymer.

Crosslinked carboxy-containing polymers are, in general, well known in the art. In a preferred embodiment such polymers may be prepared from at least about 90%, and preferably from about 95% to about 99.9% by weight, based on the total weight of monomers present, of one or more carboxy-containing monoethylenically unsaturated monomers (also occasionally referred to herein as carboxy-vinyl polymers). Acrylic acid is the preferred carboxy-containing monoethylenically unsaturated monomer, but other unsaturated, polymerizable carboxy-containing monomers, such as methacrylic acid, ethacrylic acid, .beta.-methylacrylic acid (crotonic acid), cis-.alpha.-methylcrotonic acid (angelic acid), trans-.alpha.-methylcrotonic acid (tiglic acid), .alpha.-butylcrotonic acid, .alpha.-phenylacrylic acid, .alpha.-benzylacrylic acid, .alpha.-cyclohexylacrylic acid, .beta.-phenylacrylic acid (cinnamic acid), coumaric acid (o-hydroxycinnamic acid), umbellic acid (p-hydroxycoumaric acid), and the like can be used in addition to or instead of acrylic acid.

Such polymers may be crosslinked by a polyfunctional crosslinking agent, preferably a difunctional crosslinking agent. The amount of crosslinking should be sufficient to form insoluble polymer particles, but not so great as to unduly interfere with sustained release of the active agents antibiotic. Typically the polymers are only lightly crosslinked. Preferably the crosslinking agent is contained in an amount of from about 0.01% to about 5%, preferably from about 0.1% to about 5.0%, and more preferably from about 0.2% to about 1%, based on the total weight of monomers present. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallymethacrylamide and the like. Also included are polyalkenyl polyether crosslinking agents containing two or more alkenyl ether groupings per molecule, preferably alkenyl ether groupings containing terminal $H_2C=C<$ groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053, the entire contents of which are incorporated herein by reference. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250, the entire contents of each patent being incorporated herein by reference.

The crosslinked carboxy-vinyl polymers may be made from a carboxy-vinyl monomer or monomers as the sole monoethylenically unsaturated monomer present, together with a crosslinking agent or agents. Preferably the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethylmethacrylate, 3-hydroxypropylacrylate, and the like, vinyl acetate, N-vinylpyrrolidone, and the like; see Mueller et al. U.S. Pat. No. 4,548,990 for a more extensive listing of such additional monoethylenically unsaturated monomers.

Particularly preferred polymers are lightly crosslinked acrylic acid polymers wherein the crosslinking monomer is 2,3-dihydroxyhexa-1,5-diene or 2,3-dimethylhexa-1,5-diene. Preferred commercially available polymers include polycarbophil (Noveon AA-1) and Carbopol®. Most preferably, a carboxy-containing polymer system known by the tradename DuraSite®, containing polycarbophil, which is a sustained release topical ophthalmic delivery system that releases the drug at a controlled rate, is used in the aqueous polymeric suspension composition of the present invention.

The crosslinked carboxy-vinyl polymers are preferably prepared by suspension or emulsion polymerizing the monomers, using conventional free radical polymerization catalysts, to a dry particle size of not more than about 50 μm in equivalent spherical diameter; e.g., to provide dry polymer particles ranging in size from about 1 to about 30 μm, and preferably from about 3 to about 20 μm, in equivalent spherical diameter. Using polymer particles that were obtained by mechanically milling larger polymer particles to this size is preferably avoided. In general, such polymers will have a molecular weight which has been variously reported as being from about 250,000 to about 4,000,000, and from 3,000,000,000 to 4,000,000,000.

In a more preferred embodiment of the invention for topical ophthalmic administration, the particles of crosslinked carboxy-vinyl polymer are monodisperse, meaning that they have a particle size distribution such that at least 80% of the particles fall within a 10 μm band of major particle size distribution. More preferably, at least 90%, and, most preferably at least 95%, of the particles fall within a 10 μm band of major particle size distribution. Also, a monodisperse particle size means that there is no more than 20%, preferably no more than 10%, and most preferably no more than 5% particles of a size below 1 μm. The use of a monodispersion of particles will give maximum viscosity and an increased eye residence time of the ophthalmic medicament delivery system for a given particle size. Monodisperse particles having a particle size of 30 μm and below are most preferred. Good particle packing is aided by a narrow particle size distribution.

The aqueous polymeric suspension normally contains active agents in an amount from about 0.05% to about 25%, preferably about 0.1% to about 20%, more preferably about 0.5% to about 15%, more preferably about 1% to about 12%, more preferably about 2% to about 10.0%, and polymeric suspending agent in an amount from about 0.05% to about 10%, preferably about 0.1% to about 5% and more preferably from about 0.2% to about 1.0% polymeric suspending agent. In the case of the above described water insoluble, water-swellable crosslinked carboxy-vinyl polymer, another preferred amount of the polymeric suspending agent is an amount from about 0.5% to about 2.0%, preferably about 0.5% to about 1.2%, and in certain embodiments from about 0.6% to about 0.9%, based on the weight of the composition. Although referred to in the singular, it should be understood that one or 25 more species of polymeric suspending agent, such as the crosslinked carboxy-containing polymer, can be used with the total amount falling within the stated ranges. In one preferred embodiment, the composition contains about 0.6% to about 0.8% of a polycarbophil such as NOVEON AA-1.

In one embodiment, the amount of insoluble lightly crosslinked carboxy-vinyl polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm (Brookfield Engineering Laboratories Inc.; Middleboro, Mass.). Alternatively, when the viscosity is within the range of 500 to 3000 centipoise, it may be determined by a Brookfield Model DV-11+, choosing a number cp-52 spindle at 6 rpm.

When water soluble polymers are used as the suspending agent, such as hydroxypropyl methylcellulose, the viscosity will typically be about 10 to about 400 centipoise, more typically about 10 to about 200 centipoises or about 10 to about 25 centipoise.

The stabilized active agents formulations of the instant invention containing aqueous polymeric suspensions may be formulated so that they retain the same or substantially the same viscosity in the eye that they had prior to administration to the eye. Alternatively, in the most preferred embodiments for ocular administration, they may be formulated so that there is increased gelation upon contact with tear fluid. For instance, when a stabilized formulation containing DuraSite® or other similar polyacrylic acid-type polymer at a pH of about 5.8 to about 6.8, or more preferably about 6.0 to about 6.5, or more preferably at a pH of about 6.2 to about 6.4, or more preferably about 6.25 to about 6.35, or more preferably about 6.3 is administered to the eye, the polymer will swell upon contact with tear fluid which has a higher pH. This gelation or increase in gelation leads to entrapment of the suspended active agents particles, thereby extending the residence time of the composition in the eye. The active agents are released slowly as the suspended particles dissolve over time. All these events eventually lead to increased patient comfort and increased active agents contact time with the eye tissues, thereby increasing the extent of drug absorption and duration of action of the formulation in the eye. These compositions advantageously combine stability and solubility characteristics of active agents, which display minimal degradation and relatively high solubility in aqueous compositions at the pre-administration pH, with the advantages of the gelling composition.

The viscous gels that result from fluid eye drops typically have residence times in the eye ranging from about 2 to about 12 hours, e.g., from about 3 to about 6 hours. The agents contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present.

Optional Components

In addition to the additional antibiotics that might be used, the compositions can also contain one or more of the following: surfactants, adjuvants including additional medicaments, buffers, antioxidants, tonicity adjusters, preservatives, thickeners or viscosity modifiers, and the like. Additives in the formulation may desirably include sodium chloride, EDTA (disodium edetate), and/or BAK (benzalkonium chloride), sorbic acid, methyl paraben, propyl paraben, and chlorhexidine. Other excipients compatible with various routes of administration such as topical and parenteral administration are outlined in Remington's Pharmaceutical Sciences, Mack Publishing Co., Easton, Pa., 18.sup.th edition (1990).

Representative Active Agents

The active agents, which can be present in any of the ophthalmic compositional forms described herein, including fluid and solid forms, are pharmaceutically active compounds having efficacy in ocular application.

Typically, the active agents include anesthetics, anti-inflammatory agents including steroidal and non-steroidal anti-inflammatories, antivirals, antibacterials, antifungals, and anti-allergic agents. These agents are generally present in a therapeutically effective amount, which generally is within the range of from about 0.01 to 5%, more typically 0.1 to 2%, for fluid compositions and typically from 0.5 to 50% for solid dosage forms.

In some embodiments, the compositions comprise two or more active agents, which can advantageously simplify administration and allow the treating physician to treat and/or prevent multiple conditions or symptoms simultaneously.

Anesthetics

Representative anesthetics used in ocular surgeries include tetracaine, lidocaine, marcaine, oxybuprocaine, benzocaine, butamben, dibucaine, pramoxine, proparacaine, proxymetacaine, cocaine, and Alpha-2 adrenergic receptor agonists such as Dexmedetomidine and Propofol.

Anti-Inflammatories

Steroids are one of the most commonly used medications for decreasing ocular inflammation. By inhibiting the breakdown of phospholipids into arachidonic acid, these agents act early on the inflammatory pathway. The most common side effects of this class of medications are cataract formation and glaucoma. Representative anti-inflammatory agents used for ophthalmic indications include dexamethasone, fluocinolone, loteprednol, difluprednate, fluorometholone, prednisolone, medrysone, hydrocortisone, prednisol, triamcinolone, rimexolone, and pharmaceutically-acceptable salts thereof. Drugs such as loteprednol etabonate (Lotemax; Bausch+Lomb, Rochester, N.Y.) carry a lower risk of increased IOP.1 Another new agent is difluprednate (Durezol; Sirion Therapeutics, Tampa, Fla.), which possesses even greater potency than the other available corticosteroids.

Although nonsteroidal anti-inflammatory drugs have been used to treat inflammatory conditions, physicians should exercise caution when prescribing this class of medications. In patients with severe inflammation combined with dry eye disease, treatment with non-steroidal anti-inflammatory drugs has caused corneal melting (Isawi and Dhaliwal, "Corneal melting and perforation in Stevens Johnson syndrome following topical bromfenac use," J Cataract Refract Surg. 2007; 33(9):1644-1646). In contrast, cyclosporine 0.05% (Restasis; Allergan, Inc., Irvine, Calif.) has been shown to effectively control many causes of ocular surface inflammation, and this ophthalmic emulsion has an excellent safety profile. Accordingly, direct use of cyclosporine and the combinations of active agents or active agents derivatives and cyclosporine, particularly in the form of ocular formulations such as eye drops, are also within the scope of the invention. Representative non-steroidal anti-inflammatory agents used in ophthalmic indications include Acular, Acular LS, Acuvail, Bromday, bromfenac, diclofenac, flurbiprofen, Ilevro, ketorolac, nepafenac, Nevanac, Ocufen, Prolensa, and Voltaren.

Artificial Tears for Inflammatory Treatment

If additional therapy is required, autologous serum tears can be very effective. Because they contain several important components of natural tears such as epidermal growth factor, fibronectin, and vitamin A, autologous serum tears increase the health of the ocular surface (Kojima, et al., Autologous serum eye drops for the treatment of dry eye diseases, Cornea, 27(suppl 1):S25-30 (2008)).

Antibiotic Agents

Antibiotics include beta-lactams such as penicillins (e.g., penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, and temocillin), cephalosporins (e.g., cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, and BAL9141), rifamycins (i.e., rifampicin and rifabutin), carbapenams (e.g., imipenem, ertapenem, and meropenem), and monobactams (e.g., astreonam); beta-lactamase inhibitors (e.g., clavulanate, sulbactam, and tazobactam); aminoglycosides (e.g., streptomycin, neomycin, kanamycin, paromycin, gentamicin, tobramycin, amikacin, netilmicin, spectinomycin, sisomicin, dibekalin, and isepamicin); tetracyclines (e.g., tetracycline, chlortetracycline, demeclocycline, minocycline, oxytetracycline, methacycline, and doxycycline); macrolides (e.g., erythromycin, azithromycin, and clarithromycin); ketolides (e.g., telithromycin, ABT-773); lincosamides (e.g., lincomycin and clindamycin); glycopeptides (e.g., vancomycin, oritavancin, dalbavancin, and teicoplanin); streptogramins (e.g., quinupristin and dalfopristin); sulphonamides (e.g., sulphanilamide, para-aminobenzoic acid, sulfadiazine, sulfisoxazole, sulfamethoxazole, and sulfathalidine); oxazolidinones (e.g., linezolid); quinolones (e.g., nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, and sitafloxacin); metronidazole; daptomycin; garenoxacin; ramoplanin; faropenem; polymyxin; tigecycline, AZD2563; and trimethoprim.

These antibiotics can be used in the dose ranges currently known and used for these agents, particularly when such are prescribed for treating ocular disorders. Different concentrations may be employed depending on the clinical condition of the patient, the goal of therapy (treatment or prophylaxis), the anticipated duration, and the severity of the infection for which the drug is being administered. Additional considerations in dose selection include the type of infection, age of the patient (e.g., pediatric, adult, or geriatric), general health, and co-morbidity. Determining what concentrations to employ are within the skills of the pharmacist, medicinal chemist, or medical practitioner. Typical dosages and frequencies are provided, e.g., in the Merck Manual of Diagnosis & Therapy (17th Ed. M H Beers et al., Merck & Co.).

Antiviral Agents

The most common eye infection is conjunctivitis (pinkeye) caused by an adenovirus (a type of common cold virus). Currently, antivirals are not used to treat pinkeye, but active agents such as artificial tears can be used to treat its symptoms.

Herpetic simplex keratitis is a form of keratitis caused by recurrent herpes simplex virus in cornea, and herpes simplex virus (HSV) infection is very common. Keratitis caused by HSV is the most common cause of cornea-derived blindness in developed nations.

Treatment of herpes of the eye depends on how the virus presents itself. Epithelial keratitis is caused by live virus, while stromal disease is an immune response and metaherpetic ulcer results from inability of the corneal epithelium to heal.

Epithelial keratitis is treated with topical antivirals, such as acyclovir in an ophthalmic ointment, or Valacyclovir Trifluridine, Idoxuridine or Vidarabine eye drops.

Topical corticosteroids are contraindicated in the presence of active herpetic epithelial keratitis.

Stromal keratitis is treated initially with prednisolone drops every 2 hours, accompanied by a prophylactic antiviral drug (either topical or oral, including acyclovir or valacyclovir).

Metaherpetic ulcers are treated using artificial tears and eye lubricants, stopping toxic medications, performing punctal occlusion, bandage contact lens and amniotic membrane transplant. The compositions described herein can be used to provide the non-glycosaminoglycan active pharmaceutical ingredient (API) components of artificial tears and eye lubricants in a way that maintains their presence on the eye for a relatively longer period of time than conventional formulations.

Other viral infections that can cause eye injury include varicella zoster (shingles and chickenpox) and cytomegalovirus, which doesn't affect healthy people but is the leading cause of blindness in people with AIDS. These can also be treated using appropriate antiviral agents, using the compositions described herein.

Anti-Fungal Agents

Ocular histoplasmosis syndrome (OHS, also called chorioretinitis), is caused by a fungus. It generally attacks the blood supply of the retina, on the inner rear surface of the eye. Where there is extensive maculopathy, ocular histoplasmosis is typically treated with steroids.

A fungal keratitis is an inflammation of cornea that results from infection by a fungus. Keratomycosis is the term describing the actual fungal infection of the cornea. A presumptive diagnosis of fungal keratitis is typically treated with a natamycin ophthalmic suspension, the preferred treatment for filamentous fungal infections. Fluconazole ophthalmic solution can be used for *Candida* infections of the cornea. Amphotericin B eye drops can also be used for non-responding cases.

Antiproliferative Agents

Antiproliferative Agents (also referred to as cyclostatic agents) inhibit cell growth and multiplication. These agents are frequently used in maintenance immunosuppression and treatment of rejection, as well as to treat eye diseases and infections. They can also be used to treat and/or prevent post-surgical scarring, recurrent pterygium (fleshy growth), and scarring due to PRK, lasik and superlasik procedures.

Representative antiproliferative agents include, but are not limited to, Mycophenolate Mofetil (CellCept®), Azathioprine (Imuran®), Sirolimus (Rapamune®), Tacrolimus, and Cyclosporine.

Anti-Metabolites

An anti-metabolite is a chemical that inhibits the use of a metabolite, which is another chemical that is part of normal metabolism. Such substances are often similar in structure to the metabolite they interfere with, such as the antifolates that interfere with the use of folic acid. The presence of anti-metabolites can have toxic effects on cells, such as halting cell growth and cell division, so these compounds are used as chemotherapy for cancer.

Anti-metabolites can be used in cancer treatment, as they interfere with DNA production and therefore cell division and the growth of tumors.

Anti-metabolites masquerade as a purine (azathioprine, mercaptopurine) or a pyrimidine, chemicals that become the building-blocks of DNA. They prevent these substances becoming incorporated in to DNA during the S phase (of the cell cycle), stopping normal development and division. They also affect RNA synthesis. However, because thymidine is used in DNA but not in RNA (where uracil is used instead), inhibition of thymidine synthesis via thymidylate synthase selectively inhibits DNA synthesis over RNA synthesis. Due to their efficiency, these drugs are the most widely used cytostatics.

Anti-metabolites can also function as antibiotics. For example, sulfanilamide drugs inhibit dihydrofolate synthesis in bacteria by competing with para-aminobenzoic acid.

VEGF Inhibitors

Vascular endothelial growth factor (VEGF) is a signal protein produced by cells that stimulates vasculogenesis and angiogenesis. It is part of the system that restores the oxygen supply to tissues when blood circulation is inadequate. VEGF's normal function is to create new blood vessels during embryonic development, new blood vessels after injury, muscle following exercise, and new vessels (collateral circulation) to bypass blocked vessels.

When VEGF is overexpressed, it can contribute to disease. Solid cancers cannot grow beyond a limited size without an adequate blood supply; cancers that can express VEGF are able to grow and metastasize.

Overexpression of VEGF in the eye can cause vascular disease in the retina, choroid of the eye, and age-related macular degeneration. VEGF inhibitors can inhibit VEGF, and control or slow those diseases.

Representative VEGF inhibitors include monoclonal antibodies such as bevacizumab (Avastin), antibody derivatives such as ranibizumab (Lucentis), or orally-available small molecules that inhibit the tyrosine kinases stimulated by VEGF: lapatinib (Tykerb), sunitinib (Sutent), sorafenib (Nexavar), axitinib, and pazopanib Prostaglandins Prostaglandins are a group of lipid compounds that are derived enzymatically from fatty acids, and have important functions in the animal body. Every prostaglandin contains 20 carbon atoms, including a 5-carbon ring.

Prostaglandins are mediators, and have a variety of strong physiological effects. Prostaglandins are not endocrine hormones, but autocrine or paracrine, which are locally acting messenger molecules. They differ from hormones in that they are not produced at a discrete site but in many places throughout the human body.

In ocular formulations, prostaglandins can be used as vasodilators, and to treat glaucoma. Representative prostaglandins used in ophthalmic indications include Latanaprost and Bimatoprost, a synthetic prostamide analog with ocular hypotensive activity Mitomycin C The mitomycins are a family of aziridine-containing natural products isolated from *Streptomyces caespitosus* or *Streptomyces lavendulae*. One of these compounds, mitomycin C, finds use as a chemotherapeutic agent by virtue of its antitumor and antibiotic activity.

Mitomycin C has also been used topically, rather than intravenously, in several areas, such as in eye surgery, where mitomycin C is applied topically to prevent scarring during glaucoma filtering surgery, haze after PRK or superlasik, and scarring following pterygium removal.

Antioxidants

Oxidative damage to ocular tissues can be treated and/or prevented using antioxidants. Antioxidants, such as ascorbic acid, can be used to metabolize reactive oxygen species. The topical application of antioxidants can be used, for example, to treat geographic atrophy, dry AMD, and glaucoma. The topical administration of tocotrienols is also an effective way to increase ocular tissue vitamin E concentration. The use of antioxidants to treat glaucoma is described, for example, in Zanon-Moreno et al., Antioxidant status modifications by topical administration of dorzolamide in primary open-angle glaucoma. Eur J Ophthalmol. 9(4):565-571 (2009).

TGF-Beta

Transforming growth factor beta (TGF-β) is a cytokine that controls proliferation, cellular differentiation, and other functions in most cells. TGF-β plays an important role in directing local inflammatory responses in ocular surface epithelial cells (Benito et al., "Effect of TGF-β on ocular surface epithelial cells," Exp Eye Res, 107:88-10 Feb. 2013). TGF-beta acts as an antiproliferative factor in normal epithelial cells and at early stages of oncogenesis.

TGF-beta can be topically applied to the eye, for example, to prevent recurrent ptyergium, minimize scarring following pterygium removal, and minimize scar tissue following other ocular surgeries such as PRK, lasik, or superlasik.

Combination Therapy

Because ocular infections are frequently associated with inflammation, it can be advantageous to co-administer the active agents with one or more anti-inflammatory agents. One such combination includes both active agents and dexamethasone, which can be administered in the form of a suspension, or in the form of eye drops, for topical application. Another representative corticosteroid is loteprednol etabonate.

The combination therapy can be extremely useful in connection with steroid-responsive inflammatory ocular conditions for which a corticosteroid is indicated and where bacterial infection or a risk of bacterial ocular infection exists.

Ocular steroids are indicated in inflammatory conditions of the palpebral and bulbar conjunctiva, cornea, and anterior segment of the globe, where the inherent risk of steroid use in certain infective conjunctivitis is accepted to obtain a diminution in edema and inflammation. They are also indicated in chronic anterior uveitis and corneal injury from chemical, radiation or thermal burns, or penetration of foreign bodies.

The use of a combination of antimicrobials and an anti-inflammatory agent is indicated where the risk of infection is high or where there is an expectation that potentially dangerous numbers of bacteria will be present in the eye.

III. Methods for Preparing the Compositions

Where the compositions are in the form of aqueous solutions, dispersions, or suspensions, these can be produced by simply mixing the appropriate components.

Where the compositions are in the form of ointments, these can also be produced by simply mixing the appropriate components.

The compositions can also be in freeze dried form, for reconstitution at or near the time of topical application.

IV. Methods of Providing Anesthesia for Ocular Surgery

The eye is heavily supplied by nerves, so anesthesia is essential during eye surgery. Local anesthesia is most commonly used, and the compositions described herein can be used to provide anesthesia during ocular surgeries.

Topical anesthesia using a topical gel, including an anesthetic like lidocaine, is often used for quick procedures, whereas general anesthesia is often used for children, traumatic eye injuries, major orbitotomies and for apprehensive patients. Following eye surgery, even where general anesthesia has been used, the treating physician may elect to apply a topical anesthetic so that the patient is not in pain immediately following surgery.

Representative ocular surgeries for which the compositions can be used include, but are not limited to, the following.

Laser Eye Surgery

Laser eye surgery can be used to treat non-refractive conditions (for example, to seal a retinal tear), while radial keratotomy is an example of refractive surgery that can be performed without using a laser.

Laser eye surgery, or laser corneal sculpting, is a medical procedure that uses a laser to reshape the surface of the eye to improve or correct myopia (short-sightedness), hypermetropia (long sightedness) and astigmatism (uneven curvature of the eye's surface).

Refractive Surgery

Refractive surgery aims to correct errors of refraction in the eye, reducing or eliminating the need for corrective lenses. Also, limbal relaxing incisions (LRI) can be used to correct minor astigmatism.

Keratoplasty and Keratotomy

Keratoplasty is defined as surgery performed upon the cornea, such as a corneal transplantation/grafting.

Keratotomy is a type of refractive surgical procedure, and can refer to radial keratotomy or photorefractive keratotomy.

Examples include astigmatic keratotomy (AK), also known as arcuate keratotomy or transverse keratotomy, radial keratotomy (RK), Mini Asymmetric Radial Keratotomy (M.A.R.K.), which involves preparing a series of microincisions to cause a controlled cicatrisation of the cornea, which changes its thickness and shape and can correct astigmatism and cure the first and second stage of keratoconus, and hexagonal keratotomy (HK)

Keratomilleusis

Keratomilleusis is a method of reshaping the cornea surface to change its optical power. A disc of cornea is shaved off, quickly frozen, lathe-ground, then returned to its original power. A variation of this type of operation is laser-assisted in-situ keratomileusis (LASIK), including laser-assisted sub-epithelial keratomileusis (LASEK), also known as Epi-LASIK. Similar procedures include IntraLASIK, automated lamellar keratoplasty (ALK), photorefractive keratectomy (PRK), laser thermal keratoplasty (LTK), and conductive keratoplasty (CK), which uses radio frequency waves to shrink corneal collagen and is used to treat mild to moderate hyperopia.

Cataract Surgery

A cataract is an opacification or cloudiness of the eye's crystalline lens that prevents light from forming a clear image on the retina. If visual loss is significant, surgical removal of the lens may be warranted, with lost optical power usually replaced with a plastic intraocular lens (IOL).

Glaucoma Surgery

Glaucoma is a group of diseases affecting the optic nerve that results in vision loss and is frequently characterized by raised intraocular pressure (IOP). There are many types of glaucoma surgery, and variations or combinations of those types, that facilitate the escape of excess aqueous humor from the eye to lower intraocular pressure, and a few that lower IOP by decreasing the production of aqueous humor.

Canaloplasty

Canaloplasty enhances drainage through the eye's natural drainage system to provide sustained reduction of intraocular pressure (IOP). Canaloplasty uses microcatheter technology to create a tiny incision to gain access to a canal in the eye. The microcatheter circumnavigates the canal around the iris, enlarging the main drainage channel and its smaller collector channels through the injection of a sterile, gel-like material called viscoelastic. The catheter is then removed and a suture is placed within the canal and tightened. By opening up the canal, the pressure inside the eye can be reduced.

Karmra Inlays

A Karmra inlay is placed inside the cornea, and has a small aperture that gives clearer vision at intermediate and near distances.

Scleral Reinforcement Surgery

Scleral reinforcement surgery is used to mitigate degenerative myopia.

Corneal Surgery

Corneal surgery includes most refractive surgery, as well as corneal transplant surgery, penetrating keratoplasty (PK), keratoprosthesis (KPro), phototherapeutic keratectomy (PTK), pterygium excision, corneal tattooing, osteo-odonto-keratoprosthesis (OOKP), in which support for an artificial cornea is created from a tooth and its surrounding jawbone, Vitreo-Retinal Surgery Vitreo-retinal surgery includes vitrectomies, including anterior vitrectomy, which removes the front portion of vitreous tissue to prevent or treat vitreous loss during cataract or corneal surgery, or to remove misplaced vitreous in conditions such as aphakia pupillary block glaucoma.

Pars plana vitrectomy (PPV), or trans pars plana vitrectomy (TPPV), removes vitreous opacities and membranes through a pars plana incision, and is frequently combined with other intraocular procedures for the treatment of giant retinal tears, tractional retinal detachments, and posterior vitreous detachments.

Pan retinal photocoagulation (PRP) is a type of photocoagulation therapy used in the treatment of diabetic retinopathy.

Retinal Detachment Repair

A scleral buckle is often used to repair a retinal detachment to indent or "buckle" the sclera inward, usually by sewing a piece of preserved sclera or silicone rubber to its surface. Laser photocoagulation, or photocoagulation therapy, involves using a laser to seal a retinal tear.

Pneumatic Retinopexy

Retinal cryopexy, or retinal cryotherapy, is a procedure that uses intense cold to induce a chorioretinal scar and to destroy retinal or choroidal tissue.

Eye Muscle Surgery

Eye muscle surgery typically corrects strabismus and includes transposition/repositioning procedures, tightening/strengthening procedures, loosening/weakening procedures, advancement (moving an eye muscle from its original place of attachment on the eyeball to a more forward position), recession (moving the insertion of a muscle posteriorly towards its origin), myectomy, myotomy, tenectomy, tenotomy, resection, tucking, isolating the inferior rectus muscle, disinserting the medial rectus muscle Adjustable suture surgery involves reattaching an extraocular muscle using a stitch that can be shortened or lengthened within the first post-operative day, to obtain better ocular alignment.

Surgery Involving the Lacrimal Apparatus

A dacryocystorhinostomy (DCR) or dacryocystorhinotomy restores the flow of tears into the nose from the lacrimal sac when the nasolacrimal duct does not function.

Canaliculodacryocystostomy is a surgical correction for a congenitally blocked tear duct in which the closed segment is excised and the open end is joined to the lacrimal sac.

Canaliculotomy involves slitting of the lacrimal punctum and canaliculus for the relief of epiphora.

A dacryoadenectomy is the surgical removal of a lacrimal gland.

A dacryocystectomy is the surgical removal of a part of the lacrimal sac.

A dacryocystostomy is an incision into the lacrimal sac, usually to promote drainage.

A dacryocystotomy is an incision into the lacrimal sac.

Eye removal includes enucleation, which involves removing the eye, leaving the eye muscles and remaining orbital contents intact, evisceration, which involves removing the eye's contents, leaving the scleral shell intact (usually performed to reduce pain in a blind eye), and exenteration, which involves removing the entire orbital contents, including the eye, extraocular muscles, fat, and connective tissues (usually performed to remove malignant orbital tumors).

Other Ocular Surgical Techniques

Additional surgeries include posterior sclerotomy, in which an opening is made into the vitreous through the sclera, as for detached retina or the removal of a foreign body, macular hole repair, partial lamellar sclerouvectomy, partial lamellar sclerocyclochoroidectomy, partial lamellar sclerochoroidectomy, radial optic neurotomy, macular translocation surgery, through 360 degree retinotomy, and through scleral imbrication technique.

Epikeratophakia is the removal of the corneal epithelium and replacement with a lathe cut corneal button.

Implants can be inserted, including intracorneal rings (ICRs), corneal ring segments (Intacs), implantable contact lenses, and scleral expansion bands (SEB).

Presbyopia is a condition where, with age, the eye exhibits a progressively diminished ability to focus on near objects. Presbyopia can be reversed surgically, including through anterior ciliary sclerotomy (ACS), and laser reversal of presbyopia (LRP).

A ciliarotomy is a surgical division of the ciliary zone in the treatment of glaucoma.

A ciliectomy is 1) the surgical removal of part of the ciliary body, or 2) the surgical removal of part of a margin of an eyelid containing the roots of the eyelashes.

A ciliotomy is a surgical section of the ciliary nerves.

A conjunctivoanstrostomy is an opening made from the inferior conjuctival cul-de-sac into the maxillary sinus for the treatment of epiphora.

Conjuctivoplasty is plastic surgery of the conjunctiva.

A conjunctivorhinostomy is a surgical correction of the total obstruction of a lacrimal canaliculus by which the conjunctiva is anastomosed with the nasal cavity to improve tear flow.

A corectomedialysis, or coretomedialysis, is an excision of a small portion of the iris at its junction with the ciliary body to form an artificial pupil.

A corectomy, or coretomy, is any surgical cutting operation on the iris at the pupil.

A corelysis is a surgical detachment of adhesions of the iris to the capsule of the crystalline lens or cornea.

A coremorphosis is the surgical formation of an artificial pupil.

A coreplasty, or coreoplasty, is plastic surgery of the iris, usually for the formation of an artificial pupil.

A coreoplasy, or laser pupillomydriasis, is any procedure that changes the size or shape of the pupil.

A cyclectomy is an excision of portion of the ciliary body.

A cyclotomy, or cyclicotomy, is a surgical incision of the ciliary body, usually for the relief of glaucoma.

A cycloanemization is a surgical obliteration of the long ciliary arteries in the treatment of glaucoma.

An iridectomesodialsys is the formation of an artificial pupil by detaching and excising a portion of the iris at its periphery.

An iridodialysis, sometimes known as a coredialysis, is a localized separation or tearing away of the iris from its attachment to the ciliary body.

An iridencleisis, or corenclisis, is a surgical procedure for glaucoma in which a portion of the iris is incised and incarcerated in a limbal incision.

An iridesis is a surgical procedure in which a portion of the iris is brought through and incarcerated in a corneal incision in order to reposition the pupil.

An iridocorneosclerectomy is the surgical removal of a portion of the iris, the cornea, and the sclera.

An iridocyclectomy is the surgical removal of the iris and the ciliary body.

An iridocystectomy is the surgical removal of a portion of the iris to form an artificial pupil.

An iridosclerectomy is the surgical removal of a portion of the sclera and a portion of the iris in the region of the limbus for the treatment of glaucoma.

An iridosclerotomy is the surgical puncture of the sclera and the margin of the iris for the treatment of glaucoma.

A rhinommectomy is the surgical removal of a portion of the internal canthus.

A trepanotrabeculectomy is used to treat chronic open and chronic closed angle glaucoma.

V. Treatment of Ocular Disorders with an Inflammatory Component

Some ocular disorders have an inflammatory component, such as trachoma, wet and dry age-related macular degeneration (AMD), diabetic retinopathy (DR), glaucoma, neovascular glaucoma, retinal vasculitis, uveitis, such as posterior uveitis, conjunctivitis, retinitis secondary to glaucoma, episcleritis, scleritis, optic neuritis, retrobulbar neuritis, ocular inflammation following ocular surgery, ocular inflammation resulting from physical eye trauma, cataract, ocular allergy and dry eye.

These disorders can be treated, for example, by administering one or more anti-inflammatory agents to the eye using the formulations described herein.

One example of an ocular disorder associated with inflammation is noninfectious anterior uveitis. This disorder is typically treated using corticosteroids such as prednisolone acetate (0.125% and 1% by weight), Betamethasone (1% by weight), Dexamethasone sodium phosphate (0.1% by weight in eye drops, 0.05% by weight in ointment form), Fluorometholone (0.1% and 0.25% by weight, or 0.1% in ointment form), Loteprednol, and Rimexolone (1% by weight).

The choice of topical steroid is typically made by the treating physician with respect to the severity of uveitis. Topical non-steroidal anti-inflammatory drugs (NSAIDs) like flubriprofen can also be used.

VI. Treatment of Microbial Infections

Certain ocular disorders have a microbial component, including viruses, bacteria, and fungi The compositions can be used to treat or prevent an ocular infection, including conditions of the eyelids, including blepharitis, blepharconjunctivies, meibomianitis, acute or chronic hordeolum, chalazion, dacryocystitis, dacryoadenities, and acne rosacea; conditions of the conjunctiva, including conjunctivitis, ophthalmia neonatorum, and trachoma; conditions of the cornea, including corneal ulcers, superficial and interstitial keratitis, keratoconjunctivitis, foreign bodies, and post operative infections; and conditions of the anterior chamber and uvea, including endophthalmitis, infectious uveitis, and post operative infections.

The prevention of infection includes pre-operative treatment prior to surgery as well as other suspected infectious conditions or contact. Examples of prophylaxis situations include treatment prior to surgical procedures such as blepharoplasty, removal of chalazia, tarsorrhapy, procedures for the canualiculi and lacrimal drainage system and other operative procedures involving the lids and lacrimal apparatus; conjunctival surgery including removal of ptyregia, pingueculae and tumors, conjunctival transplantation, traumatic lesions such as cuts, burns and abrasions, and conjunctival flaps; corneal surgery including removal of foreign bodies, keratotomy, and corneal transplants; refractive surgery including photorefractive procedures; glaucoma surgery including filtering blebs; paracentesis of the anterior chamber; iridectomy; cataract surgery; retinal surgery; and procedures involving the extra-ocular muscles. The prevention of ophthalmia neonatorum is also included.

The antibiotics described herein can be used to treat or prevent infections, including ocular infections caused by a variety of bacteria or parasites, including but not limited to one or more of the following organisms: *Staphylococcus* including *Staphylococcus aureus* and *Staphylococcus epidermidis*; *Streptococcus* including *Streptococcus pneumoniae* and *Streptococcus pyogenes* as well as Streptococci of Groups C, F, and G and *Viridans* group of Streptococci; *Haemophilus* influenza including biotype III (*H. Aegyptius*); *Haemophilus ducreyi*; *Moraxella catarrhalis*; *Neisseria* including *Neisseria gonorrhoeae* and *Neisseria meningitidis*; *Chlamydia* including *Chlamydia trachomatis*, *Chlamydia psittaci*, and *Chlamydia pneumoniae*; *Mycobacterium* including *Mycobacterium tuberculosis* and *Mycobacterium avium*-intracellular complex as well as a typical *mycobacterium* including *M. marinum*, *M. fortuitm*, and *M. chelonae*; *Bordetella pertussis*; *Campylobacter jejuni*; *Legionella pneumophila*; *Bacteroides bivius*; *Clostridium perfringens*; *Peptostreptococcus* species; *Borrelia burgdorferi*; *Mycoplasma pneumoniae*; *Treponema pallidum*; *Ureaplasma urealyticum*; *toxoplasma*; *malaria*; and *nosema*.

Some of the more common genera found are *Haemophilus, Neisseria, Staphylococcus, Streptococcus*, and *Chlamydia*. As many of these bacteria are associated with a "cryptic" phase, it can be extremely difficult to treat these infections using conventional antibiotic therapy. However, because the compositions described herein maintain the active agents in contact with the eye for an extended period of time, they are ideally suitable for treating such bacterial infections, as they can help maintain a local concentration of antibiotic in the eye long enough to treat bacteria when they emerge from the cryptic phase.

Specific types of ocular disorders that can be treated or prevented by the active agents-containing compositions include, but are not limited to, the following:

Trachoma

*Trachomatis* is an infectious eye disease, and the leading cause of the world's infectious blindness. Globally, 84 million people suffer from active infection and nearly 8 million people are visually impaired as a result of this disease.

Trachoma is caused by *Chlamydia trachomatis* and it is spread by direct contact with eye, nose, and throat secretions from affected individuals, or contact with fomites (inanimate objects), such as towels and/or washcloths, that have had similar contact with these secretions. Flies can also be a route of mechanical transmission. Untreated, repeated trachoma infections result in entropion—a painful form of permanent blindness when the eyelids turn inward, causing the eyelashes to scratch the cornea.

The bacterium has an incubation period of 5 to 12 days, after which the affected individual experiences symptoms of conjunctivitis, or irritation similar to "pink eye." Blinding endemic trachoma results from multiple episodes of re-infection that maintains the intense inflammation in the conjunctiva. Without re-infection, the inflammation will gradually subside.

The conjunctival inflammation is called "active trachoma" and usually is seen in children, especially pre-school children. It is characterized by white lumps in the undersurface of the upper eye lid (conjunctival follicles or lymphoid germinal centers) and by non-specific inflammation and thickening often associated with papillae. Follicles may also appear at the junction of the cornea and the sclera (limbal follicles). Active trachoma will often be irritating and have a watery discharge. Bacterial secondary infection may occur and cause a purulent discharge.

The later structural changes of trachoma are referred to as "cicatricial trachoma". These include scarring in the eye lid (tarsal conjunctiva) that leads to distortion of the eye lid with buckling of the lid (tarsus) so the lashes rub on the eye (trichiasis). These lashes will lead to corneal opacities and scarring, and then to blindness.

The compositions described herein can be used prophylactically to prevent the spread of infection, for example, in poor communities where infection has already occurred, and is likely to spread.

In one embodiment, one can administer drops of the stabilized solutions described herein to the eyes of individuals suffering from, or at risk from suffering from, a *C. trachomatis* infection in their eyes. In another embodiment, active agents are administered orally to a patient suffering from trachoma, typically in a dosage range of around 25 mg, and, ideally, administered in only one or two doses.

Bacterial Conjunctivitis

Bacterial conjunctivitis is a purulent infection of the conjunctiva by any of several species of gram-negative, gram-positive, or acid-fast organisms. Some of the more commonly found genera causing conjunctival infections are *Haemophilus, Streptococcus, Neisseria*, and *Chlamydia*.

Hordeolum

Hordeolum is a purulent infection of one of the sebaceous glands of Zeis along the eyelid margin (external) or of the meibomian gland on the conjunctival side of the eyelid (internal).

Infectious Keratoconjunctivitis

Infectious keratoconjunctivitis is an infectious disease of cattle, sheep, and goats, characterized by blepharospasm, lacrimation, conjunctivitis, and varying degrees of corneal opacity and ulceration. In cattle the causative agent is *Moraxella bovis*; in sheep, *mycoplasma, rickettsia, Chlamydia*, or *acholeplasma*, and in goats, *rickettsia*.

Ocular Tuberculosis

Ocular tuberculosis is an infection of the eye, primarily the iris, ciliary body, and choroid.

Uveitis

Uveitis is the inflammatory process that involves the uvea or middle layers of the eye. The uvea includes the iris (the colored part of the eye), the choroid (the middle blood vessel layer) and the ciliary body—the part of the eye that joins both parts. Uveitis is the eye's version of arthritis. The most common symptoms and signs are redness in the white part of the eye, sensitivity to light, blurry vision, floaters, and irregular pupil. Uveitis can present at any age, including during childhood.

Uveitis is easily confused with many eye inflammations, such as conjunctivitis (conjunctival inflammation) or pink eye; keratitis (corneal inflammation); episleritis or scleritis (blood vessel inflammation in the episclera or sclera respectively); or acute closed angle glaucoma.

Suppurative Uveitis

Suppurative uveitis is an intraocular infection caused mainly by pus-producing bacteria, and rarely by fungi. The infection may be caused by an injury or surgical wound (exogenous) or by endogenous septic emboli in such diseases as bacterial endocarditis or meningococcemia.

Blepharatis

Nonspecific conjunctivitis (NSC) has many potential causes, including fatigue and strain, environmental dryness and pollutants, wind and dust, temperature and radiation, poor vision correction, contact lens use, computer use and dry eye syndrome. Another cause relates to the body's innate reaction to dead cells, which can cause nonspecific conjunctivitis.

This type of infection can occur when a patient's lid disease causes mild conjunctivitis, and dead Staphylococcal bacteria from the lids fall onto the ocular surface. The cells trigger an inflammatory hypersensitivity reaction on the already irritated eyes. This inflammatory reaction against the dead cells can be treated using an anti-inflammatory agent to combat inflammation and the active agents or active agents derivatives described herein to address the potential for any living Staph bacteria.

Aside from allergy, the combined causes of inflammation and infection are probably the most common origins of conjunctivitis. In fact, this combination is more common than all types of infection combined. The concentration of mast cells in the conjunctiva and the eyelids makes them prime targets for hypersensitivity reactions and inflammatory disease. A compromised ocular surface cannot protect itself from bacteria with full efficacy. Although NSC patients may not have full-blown bacterial infections, their eyes are susceptible to some bacterial disease components.

Unlike patients with allergic conjunctivitis, who are typically treated using steroids alone, or patients who need a strong antibiotic for bacterial disease, NSC patients can benefit from a combination treatment (active agents and an anti-inflammatory agent) to battle inflammatory NSC.

Corneal Inflammation

Corneal inflammation is one of the most common ocular diseases in both humans and animals and can lead to blindness or even cause lost of the eye itself. In humans, keratitis is classified into infectious and non-infectious, while in veterinary medicine the tradition is to classify keratitis rather into ulcerative and non-ulcerative (Whitley and Gilger 1999). Non-ulcerative keratitis in dogs is usually caused by mechanical irritation (pigmentary keratitis) or by immune-mediated process (pannus). However, non-ulcerative infectious keratitis also exists (corneal abscess, mycotic, viral keratitis). Ulcerative keratitis can be of non-infectious (recurrent erosions, traumatically induced superficial ulceration) or infectious (bacterial, viral, mycotic) origin. Even in the cases of originally non-infectious ulceration, after disruption in the epithelium secondary infection often occurs.

VII. Miscellaneous Treatment and Prevention of Ocular Disorders

As discussed elsewhere herein, antiproliferative agents (also referred to as cyclostatic agents) inhibit cell growth and multiplication, and can be applied topically to the eye to treat eye diseases and infections, and to treat and/or prevent post-surgical scarring, recurrent pterygium (fleshy growth), and scarring due to PRK, lasik and superlasik procedures.

Anti-metabolites can also be topically administered to the eye, and function as antibiotics.

VEGF inhibitors can be topically administered to the to treat or prevent vascular disease in the retina, choroid of the eye, and age-related macular degeneration.

Prostaglandins can be topically administered to the eye and used as vasodilators, and to treat or prevent glaucoma.

Mitomycin C can be topically applied to the eye to prevent scarring during glaucoma filtering surgery, haze after PRK or superlasik, and scarring following pterygium removal.

Antioxidants can be topically applied to treat geographic atrophy, dry AMD, and glaucoma.

TGF-beta can be topically applied to the eye, for example, to prevent recurrent ptyergium, minimize scarring following pterygium removal, and minimize scar tissue following other ocular surgeries such as PRK, lasik, or superlasik.

Any and all of these disorders can be treated or prevented using the compositions described herein, when an appropriate pharmaceutically active agent is used to treat the specific type of condition.

The present invention will be better understood with reference to the following non-limiting examples. In these examples, all of the percentages recited herein refer to weight percent, unless otherwise indicated.

EXAMPLE 1

Delivery of an Ophthalmic Anesthetic

Background:

Tetracaine Hydrochloride is the most frequently utilized ophthalmic anesthetic in the United States and it's currently available as a 0.5% ophthalmic solution. It is commonly used for procedures in which a rapid and short acting topical ophthalmic anesthetic. It is also commonly used in cataract procedures. Typically, because it's short duration of action it is applied during the surgical procedure and may require multiple applications during surgery.

Tetracaine acts by decreasing the permeability of the neuronal membrane, thereby decreasing the flux of sodium, potassium and other ions associated with propagation of the nerve impulse. The onset of anesthesia usually begins within 30 seconds and lasts a relatively short period of time Formulation:

Activities were performed to improve the profile for anesthesia specifically looking to increase the duration of action.

This rabbit study was performed in order to evaluate various formulations. General guidelines for these studies are attached here as Attachment 1. This guideline defines the screening of six (6) formulations using two (2) different viscosity enhancing agents. The two agents selected were Carboxymethylcellulose (CMC) and Sodium Hyluronate (HA). The specifics of these formulations are described in Attachment 2.

A statistical analysis of the experimental results for both onset of action and the duration of anesthesia is provided below. The means were compiled and statistically compared to the controls in each individual formulation. The significance or non-significance is noted as (S=Significant P value <0.001, NS=Not Significant P Value >0.05). The duration results are summarized here in Table 1. The onset of action showed no statistically significant differences from the controls for all formulations.

TABLE 1

Impact of Viscosity Enhancing Agents on Duration of Anesthesia

| Mercer Sample ID | Polymer | Polymer Conc. | Viscosity | Duration (Mean) | Significance |
|---|---|---|---|---|---|
| Sample 1 | CMC | 0.50 | 47 | 17.6 | NS |
| Sample 2 | CMC | 1.00 | 356 | 22.6 | NS |
| Sample 3 | CMC | 2.00 | >1000 | 43.8 | S |
| Sample 4 | HA | 0.50 | 267 | 42.3 | S |
| Sample 5 | HA | 1.00 | 937 | 55.5 | S |
| Sample 6 | HA | 0.75 | 648 | 53.2 | S |
| Control | Alcon | 0 | <5 | 12.4 | NA |

* Greater than 1000 cps

HA and CMC molecular weights and other formulation components are listed in Attachment 2.

Several findings are worthy of note in this evaluation.

Surprisingly, a direct relationship between viscosity and improvement in the duration of efficacy is not maintained. The carboxymethylcellulose (CMC) products do not perform as well as hyaluronic acid (HA) formulations with similar viscosities.

The improvement in the duration of efficacy using HA is clearly superior to that of CMC. (Note: While the viscosities of formulations 2 and 4 are similar range, the slightly lower viscosity formulation 4 has near double the mean duration of action).

As the viscosity increases the duration of action improves for the CMC containing formulations. Notably, the viscosity required to show a statistically significant difference from the control was noted in the rabbit study as being "too viscous" to be practically applied.

Surprisingly, while there is improvement with increases in viscosity using HA from the 0.5% concentration to the 0.75% concentration. There is no notable improvement between 0.75% and 1.0% HA even though the viscosity increases.

Table 2 is below a compilation of the data for the CMC formulations.

TABLE 2

The Effect of CMC Concentration on Viscosity and Duration of Action for Tetracaine

| Polymer | Amount (w/w %) | Lot Number | Viscosity (cps) | Duration (Min.) |
|---|---|---|---|---|
| Control | 0 | NA | <5 | 12.4 |
| CMC | 0.50 | 1108576 | 47 | 17.6 |
| CMC | 1.00 | 1108576 | 356 | 22.6 |
| CMC | 2.00 | 1108576 | >1000 | 43.8 |

Table 3 is a compilation of the data for the HA formulations.

TABLE 3

The Effect of CMC Concentration on Viscosity and Duration of Action for Tetracaine

| Polymer | Amount (w/w %) | Lot Number | Viscosity (cps) | Duration (Min.) |
|---|---|---|---|---|
| Control | 0 | NA | <5 | 12.4 |
| HA | 0.50 | 861207 | 267 | 42.3 |
| HA | 0.75 | 861207 | 648 | 53.2 |
| HA | 1.00 | 861207 | 937 | 55.5 |

Summary:

The tetracaine extended release formulation described in this example uses hyaluronic acid to increase the viscosity, and thus extend the duration of anesthesia. The present inventor has discovered that viscosity was not the only factor in extending ocular anesthesia. Indeed, formulations using CMC tended to have higher viscosities than their HA counterparts. Surprisingly, the higher viscosities of CMC did not result in better duration of action when compared to the HA counterparts.

An additional surprising result was discovered during an in-vivo evaluation that a formulation containing 0.75% hyaluronic acid was equivalent to a higher viscosity 1.0% formulation hyaluronic acid formulation. Because one would normally expect that increased viscosity provides longer anesthesia, this was a surprising result.

EXAMPLE 2

Evaluation of Tetracaine Formulations in Rabbits

Background:

Currently tetracaine is commonly used in ocular surgical procedures. In the case of cataract surgery the anesthetic properties of the drug are initiated in minutes and last approximately 15-20 minutes. This often requires the reapplication of the anesthetic two to three times during the surgical procedure. To avoid the requirement for multiple reapplications a formulation with similar or shorter onset of action, a longer acting product is desired for such surgical procedures.

Purpose:

To determine the impact of various formulation improvements on the initiation and duration of anesthetic effect of Tetracaine:

Formulations Tested:

Six different formulations were tested and the onset and duration of action was evaluated.

The commercially available Tetracaine hydrochloride 0.5% Ophthalmic Solution was used as the control.

Animals Experimentation and Dosing Regimen:

New Zealand White Rabbits were obtained from Harlan Sprague Dawley. They were housed in the animal facility at Mercer University's College of Pharmacy & Health Sciences facility in Atlanta. Rabbits were quarantined for a period of 10 days before use.

Dosing was performed with the experimental formulation in one eye by dropping the formulation into the rabbit eye with the aid of a dropper and the standard marketed product was administered in the contra lateral eye as a control. Multiple experiments were run with the same group of rabbits. A washout period of 5-8 days between experiments was utilized. Rabbits received different formulations each time the experiment was repeated.

Observation/Response:

The response to surface stimulation was evaluated over a period of 1.5 hour or until the subject showed a positive blink response for two consecutive measurements.

The results of the experiments for the CMC Formulations (TCMC 0.5, TCMC 1.0, TCMC2.0) are noted in TABLE 4. The results of the experiments for the HA Formulations (THA0.5, THA0.75, THA1.0) are noted in TABLE 5

Other Observations

No signs of ocular irritation or ocular response such as lacramation were observed in any of the animals during the study period.

TABLE 4

BLINK RESPONSE DATA

| Rabbit Number | Sample 1 (TCMC 0.5) | | | | Sample 2 (TCMC 1.0) | | | | Sample 3* (TCMC 2.0) | | | |
|---|---|---|---|---|---|---|---|---|---|---|---|---|
| | Onset (min) | | Duration (min) | | Onset (min) | | Duration (min) | | Onset (min) | | Duration (min) | |
| | SN 1 | Control | SN 1 | Control | SN 2 | Control | SN 2 | Control | SN 3 | Control | SN 3 | Control |
| Rabbit 1 | | | | | 9 | 10 | 21 | 5 | 10 | 10 | 40 | 15 |
| Rabbit 2 | 5 | 5 | 35 | 15 | | | | | 6 | 6 | 49 | 9 |
| Rabbit 3 | 15 | 10 | 15 | 12 | 5 | 5 | 30 | 10 | | | | |
| Rabbit 4 | 8 | 6 | 10 | 14 | 10 | 5 | 20 | 15 | 35 | 35 | 50 | 5 |
| Rabbit 5 | 10 | 10 | 5 | 2.5 | 25 | 8 | 10 | 12 | 15 | 15 | 35 | 10 |
| Rabbit 6 | 9 | 8 | 6 | 7 | 13 | 13 | 15 | 10 | 25 | 25 | 25 | 5 |
| Mean SEM | 9.4 | 7.8 | 14.2 | 10.1 | 12.4 | 8.2 | 19.2 | 10.4 | 18.2 | 13.2 | 39.8 | 8.8 |

*Very Viscous

TABLE 5

BLINK RESPONSE DATA

| Rabbit Number | Sample 4 (THA 0.5) | | | | Sample 5 ** (THA 1.0) | | | | Sample 6 (THA 0.75) | | | |
|---|---|---|---|---|---|---|---|---|---|---|---|---|
| | Onset (min) | | Duration (min) | | Onset (min) | | Duration (min) | | Onset (min) | | Duration (min) | |
| | SN 4 | Control | SN 4 | Control | SN 5 | Control | SN 5 | Control | SN 6 | Control | SN 6 | Control |
| Rabbit 1 | 3 | 9 | 67 | 16 | 15 | 10 | 40 | 15 | 2 | 10 | 123 | 5 |
| Rabbit 2 | 2 | 3 | 48 | 22 | 5 | 5 | 55 | 15 | 2 | 10 | 43 | 15 |
| Rabbit 3 | 25 | 10 | 15 | 10 | ***35 | 3 | 40 | 7 | 7 | 9 | 58 | 16 |
| Rabbit 4 | 6 | 20 | 24 | 5 | 5 | 10 | 30 | 10 | 15 | 8 | 40 | 12 |
| Rabbit 5 | 5 | 5 | 75 | 15 | 6 | 15 | 64 | 15 | 10 | 8 | 45 | 17 |
| Rabbit 6 | 10 | 7 | 25 | 13 | 5 | 5 | 135 | 15 | 10 | 7 | 45 | 13 |
| Rabbit 7 | 20 | 20 | 30 | 10 | 4 | 15 | 56 | 15 | 3 | 15 | 37 | 10 |
| Rabbit 8 | 4 | 4 | 36 | 5 | 6 | 10 | 59 | 15 | 4 | 10 | 31 | 10 |
| Rabbit 9 | 8 | 10 | 47 | 15 | 10 | 15 | 30 | 5 | 9 | 10 | 61 | 10 |
| Rabbit 10 | 9 | 15 | 31 | 15 | 4 | 9 | 46 | 16 | 9 | 4 | 51 | 16 |
| Rabbit 11 | 9 | 15 | 46 | 5 | 10 | 9 | 40 | 21 | 4 | 10 | 56 | 25 |
| Rabbit 12 | 15 | 15 | 15 | 10 | 4 | 15 | 71 | 10 | 7 | 10 | 48 | 10 |
| Mean SEM | 9.667 | 11.08 | 42.33 | 11.75 | 6.727 | 10.08 | 55.5 | 13.25 | 6.833 | 9.25 | 53.17 | 12.42 |

** Viscous
***animal could not open eye since the eye drops touched the eyelids

TABLE 6

| | Sample Identification | |
|---|---|---|
| Product ID | Pre-clinical Study ID | Inventor ID |
| (TCMC 0.5) | Sample 1 | IEPS-081-016-A |
| (TCMC 1.0) | Sample 2 | EPS-081-016-B |
| (TCMC 2.0) | Sample 3 | EPS-081-016-C (* very viscous) |
| (THA 0.50) | Sample 4 | EPS-081-016-D |

TABLE 6-continued

| | Sample Identification | |
|---|---|---|
| Product ID | Pre-clinical Study ID | Inventor ID |
| (THA 1.0) | Sample 5 | EPS-081-017-B (** viscous) |
| (THA 0.75) | Sample 6 | EPS-081-13-B |

The specific details of these formulations are provided in attachments 1 and 2

EXAMPLE 3

Evaluation of Tetracaine Formulations in Rabbits

General Observations and Comments:
Statistical Analysis:
The statistical analyses conducted are listed in Table 6 and Table 7.
Time Sequence of Drug Administration:
The time between subsequent drug administrations are listed in Table 7 and Table 8. The number of days represents the washout time in between subsequent drug administration. The letters in caps, L or R represents the left or right eye tested with the drug formulation.

TABLE 7

Blink Response

Sample 1 (TCMC 0.5)

| | | Order | | Onset | | Duration |
|---|---|---|---|---|---|---|
| RN | Eye | WO | SN 1 | Control | SN 1 | Control |
| 1 | | | | | | |
| 2 | L | 6 | 5 | 5 | 40 | 20 |
| 3 | L | 6 | 15 | 10 | 20 | 10 |
| 4 | L | 6 | 8 | 10 | 12 | 5 |
| 5 | L | initial | 10 | 10 | 5 | 5 |
| 6 | L | 6 | 9 | 8 | 11 | 12 |
| Mean | | | 9.4 | 8.6 | 17.6 | 10.4 |
| P-Value | | | >0.05 NS | | >0.05 NS | |

Sample 2 (TCMC 1.0)

| | | Order | | Onset | | Duration |
|---|---|---|---|---|---|---|
| RN | Eye | WO | SN 2 | Control | SN 2 | Control |
| 1 | L | 6 | 9 | 10 | 26 | 10 |
| 2 | | | | | | |
| 3 | L | initial | 5 | 5 | 35 | 15 |
| 4 | L | 6 | 10 | 5 | 25 | 20 |
| 5 | L | 6 | 25 | 8 | 10 | 12 |
| 6 | L | 6 | 13 | 13 | 17 | 12 |
| Mean | | | 12.4 | 8.2 | 22.6 | 13.8 |
| P-Value | | | >0.05 NS | | >0.05 NS | |

Sample 3 (TCMC 2.0)

| | | Order | | Onset | | Duration |
|---|---|---|---|---|---|---|
| RN | Eye | WO | SN 3 | Control | SN 3 | Control |
| 1 | L | 6 | 10 | 10 | 45 | 15 |
| 2 | L | 6 | 6 | 6 | 49 | 14 |
| 3 | | | | | | |
| 4 | L | initial | 35 | 10 | 50 | 10 |
| 5 | L | 6 | 15 | 5 | 40 | 15 |
| 6 | L | 6 | 25 | 20 | 30 | 10 |
| Mean | | | 18.2 | 10.2 | 43.8 | 12.8 |
| P-Value | | | >0.05 NS | | <0.05 S | |

S = significant,
NS = not significant
RN = Rabbit Number
WO = Washout Period (min)
R = Right Eye;
L = Left Eye
* Very Viscous

TABLE 8

Blink Response (Sample 4 (THA 0.5))

| | | Order | | Onset | | Duration |
|---|---|---|---|---|---|---|
| RN | Eye | WO | SN 4 | Control | SN 4 | Control |
| 1 | R | 1 | 3 | 9 | 67 | 16 |
| 2 | L | 6 | 2 | 3 | 48 | 22 |
| 3 | L | 6 | 25 | 10 | 15 | 10 |
| 4 | L | 6 | 6 | 20 | 24 | 5 |
| 5 | L | NA | 5 | 5 | 75 | 15 |
| 6 | L | 6 | 10 | 7 | 25 | 13 |
| 1B | R | 7 | 20 | 20 | 30 | 10 |
| 2B | R | 7 | 4 | 4 | 36 | 5 |
| 3B | L | 7 | 8 | 10 | 47 | 15 |
| 4B | L | 7 | 9 | 15 | 31 | 15 |
| 5B | L | 7 | 9 | 15 | 46 | 5 |
| 6B | L | 7 | 15 | 15 | 15 | 10 |
| Mean | | | 9.7 | 11.1 | 42.3 | 11.8 |
| P-Value | | | >0.05 NS | | <0.001 S | |
| P-Value | | | >0.05 NS | | <0.001 S | |

Sample 5 ** (THA 1.0)

| | | Order | | Onset | | Duration |
|---|---|---|---|---|---|---|
| RN | Eye | WO | SN 5 | Control | SN 5 | Control |
| 1 | R | 7 | 15 | 10 | 40 | 15 |
| 2 | L | 6 | 5 | 5 | 55 | 15 |
| 3 | L | 6 | ***35 | 3 | 40 | 7 |
| 4 | L | 6 | 5 | 10 | 30 | 10 |
| 5 | L | 6 | 6 | 15 | 64 | 15 |
| 6 | L | NA | 5 | 5 | 135 | 15 |
| 1B | L | 7 | 4 | 15 | 56 | 15 |
| 2B | L | 7 | 6 | 10 | 59 | 15 |
| 3B | L | 7 | 10 | 15 | 30 | 5 |
| 4B | L | 7 | 4 | 9 | 46 | 16 |
| 5B | R | 7 | 10 | 9 | 40 | 21 |
| 6B | R | 7 | 4 | 15 | 71 | 10 |
| Mean | | | 9.1 | 10.1 | 55.5 | 13.3 |

Sample 6 (THA 0.75)

| | | Order | | Onset | | Duration |
|---|---|---|---|---|---|---|
| RN | Eye | WO | SN 6 | Control | SN 6 | Control |
| 1 | L | 6 | 2 | 10 | 123 | 5 |
| 2 | L | 6 | 2 | 10 | 43 | 15 |
| 3 | L | 6 | 7 | 9 | 58 | 16 |
| 4 | R | 7 | 15 | 8 | 40 | 12 |
| 5 | R | 7 | 10 | 8 | 45 | 17 |
| 6 | R | 7 | 10 | 7 | 45 | 13 |
| 1B | L | 7 | 3 | 15 | 37 | 10 |
| 2B | L | 7 | 4 | 10 | 31 | 10 |
| 3B | R | 7 | 9 | 10 | 61 | 10 |
| 4B | R | 7 | 9 | 4 | 51 | 16 |
| 5B | L | 7 | 4 | 10 | 56 | 15 |
| 6B | L | 7 | 7 | 10 | 48 | 10 |
| Mean | | | 6.8 | 9.3 | 53.2 | 12.4 |
| P-Value | | | >0.05 NS | | <0.001 S | |

S = significant,
NS = not significant
RN = Rabbit Number
WO = Washout Period (min)
R = Right Eye;
L = Left Eye
* Very Viscous
***animal could not open eye since the eye drops touched the eyelids The present invention is not to be limited in scope by the specific embodiments described herein. Indeed, various modifications of the invention in addition to those described will become apparent to those skilled in the art from the foregoing description. Such modifications are intended to fall within the scope of the appended claims.

Various publications are cited herein, the disclosures of which are incorporated by reference in their entireties.

The invention claimed is:

1. A topical composition for application to the eye, comprising hyaluronic acid in a concentration effective to achieve a viscosity in the range of 350 cps to 50,000 cps, water, and an anesthetic selected from the group consisting of tetracaine, lidocaine, marcaine, oxybuprocaine, benzocaine, dibucaine, proparacaine, proxymetacaine, cocaine, and pharmaceutically-acceptable salts thereof.

2. A topical composition for application to the eye, comprising a glycosaminoglycan in a concentration effective to achieve a viscosity in the range of 350 cps to 5,000 cps, water, and an anesthetic selected from the group consisting of tetracaine, lidocaine, marcaine, oxybuprocaine, benzocaine, dibucaine, proparacaine, proxymetacaine, cocaine, and pharmaceutically-acceptable salts thereof.

3. The composition of claim 1, wherein the hyaluronic acid is present in a concentration between about 0.35 and about 1.0 percent by weight.

4. The composition of claim 2, wherein the hyaluronic acid is present in a concentration between about 0.5 and about 0.9 percent by weight.

5. The composition of claim 2, wherein the hyaluronic acid is present in a concentration between about 0.6 and about 0.75 percent by weight.

6. The composition of claim 1, wherein the carrier is in the form of eye drops or other topical formulations for direct administration to the eye.

7. The composition of claim 1, where in the pH of the formulation is adequate to provide for an acceptable product for the delivery of the active agent to the ocular surface.

8. The composition of claim 1, wherein two or more active agents are present.

9. A method of providing anesthesia before, during, or after ocular surgery, comprising topically administering a composition of claim 2 to a patient in need thereof before, during, or after ocular surgery.

10. The composition of claim 1 wherein the anesthetic is tetracaine.

11. The composition of claim 10 wherein the concentration of tetracaine is between 0.1% and 1.0%.

12. A topical composition for application to the eye, consisting essentially of hyaluronic acid in a concentration effective to achieve a viscosity in the range of 350 cps to 50,000 cps, water, and an anesthetic selected from the group consisting of tetracaine, lidocaine, marcaine, oxybuprocaine, benzocaine, dibucaine, proparacaine, proxymetacaine, cocaine, and pharmaceutically-acceptable salts thereof.

13. A topical composition for application to the eye, consisting essentially of a glycosaminoglycan in a concentration effective to achieve a viscosity in the range of 350 cps to 50,000 cps, water, and an anesthetic selected from the group consisting of tetracaine, lidocaine, marcaine, oxybuprocaine, benzocaine, dibucaine, proparacaine, proxymetacaine, cocaine, and pharmaceutically-acceptable salts thereof.

14. The composition of claim 1, wherein the viscosity is in the range of 350 to 7600 cps, and the anesthetic is in the form of a pharmaceutically-acceptable salt.

15. The composition of claim 2, wherein the viscosity is in the range of 350 to 7600 cps, and the anesthetic is in the form of a pharmaceutically-acceptable salt.

16. The composition of claim 12, wherein the viscosity is in the range of 350 to 7600 cps, and the anesthetic is in the form of a pharmaceutically-acceptable salt.

17. The composition of claim 13, wherein the viscosity is in the range of 350 to 7600 cps, and the anesthetic is in the form of a pharmaceutically-acceptable salt.

* * * * *